(12) United States Patent
Forssmann et al.

(10) Patent No.: US 6,809,175 B1
(45) Date of Patent: Oct. 26, 2004

(54) CADHERIN DERIVED GROWTH FACTOR AND ITS USE

(75) Inventors: Wolf-Georg Forssmann, Hannover (DE); Ludger Standker, Hannover (DE); Markus Meyer, Hannover (DE); Hossein Mostafavi, Hannover (DE); Hans-Georg Opitz, Weinheim (DE); Lothar Kling, Mannheim (DE)

(73) Assignee: Prof. Dr. Wolf-Georg Forssmann, Hannover (DE)

( * ) Notice: Subject to any disclaimer, the term of this patent is extended or adjusted under 35 U.S.C. 154(b) by 0 days.

(21) Appl. No.: 09/509,559

(22) PCT Filed: Oct. 15, 1998

(86) PCT No.: PCT/EP98/06547

§ 371 (c)(1),
(2), (4) Date: Nov. 27, 2000

(87) PCT Pub. No.: WO99/19477

PCT Pub. Date: Apr. 22, 1999

(30) Foreign Application Priority Data

Oct. 15, 1997 (DE) .......................................... 197 45 284
Mar. 25, 1998 (DE) .......................................... 198 13 088

(51) Int. Cl.⁷ ........................ C07K 14/00; C07K 14/51; A61K 38/00; C12N 15/00
(52) U.S. Cl. .......................... 530/300; 512/2; 530/344; 530/333; 435/69.1
(58) Field of Search .................................. 530/300, 344, 530/333; 514/2; 435/69.1; 536/23.5

(56) References Cited

U.S. PATENT DOCUMENTS 5,646,250 A    7/1997  Suzuki 5,869,638 A  *  2/1999  Takeshita et al. .......... 536/23.5

FOREIGN PATENT DOCUMENTS

EP    0 585 801 A2    3/1994

OTHER PUBLICATIONS

Well, J. A. Additivity of Mutational Effects in Proteins. Biochemistry 29:8509–8517 (1990).*

Hidenobu Tanhara et al., "Clonging of Five Human Cadherins Clarifies Characteristic Features of Cadherin Extracellular Domain and Provides Further Evidence for Two Structurally Different Types of Cadherin", Cell Adhesion and Communication, vol. 2, Jan. 1, 1994, pp. 15–26.

Sara Selig et al., "Molecular Characterization of Br–Cadherin, a Developmentally Regulated Brain–Specific Cadherin", Proceedings of the National Academy of Sciences of USA. vol. 94, No. 6 Mar. 18, 1997, pp. 2398–2403.

* cited by examiner

*Primary Examiner*—Gary Kunz
*Assistant Examiner*—Regina M. DeBerry
(74) *Attorney, Agent, or Firm*—Jacobson Holman PLLC

(57) ABSTRACT

A peptide referred to as cadherin-derived growth factor (CDGF) the sequence of which corresponds to a partial sequence of a pre-pro-cadherin, said pre-pro-cadherin comprising the domains signal sequence, pro sequence cadherin repeats, transmembrane region and intracellular domain, characterized in that the sequence of said peptide comprises the pro sequence, that at least one of the other domains of the pre-pro-cadherin is lacking, and that said peptide has cell-proliferative, cell-protective and/or cell-differential properties.

6 Claims, 7 Drawing Sheets

SEQUENCE LISTING

<160> NUMBER OF SEQ ID NOS: 14

<210> SEQ ID NO 1
<211> LENGTH: 123
<212> TYPE: PRT
<213> ORGANISM: Homo sapiens

<400> SEQUENCE: 1

Cys His Pro Gly Phe Asp Ala Glu Ser Tyr Thr Phe Thr Val Pro Arg

-continued

```
                1               5              10              15
Arg His Leu Glu Arg Gly Arg Val Leu Gly Arg Val Asn Phe Cys Thr
                    20                          25                          30
Gly Arg Gln Arg Thr Ala Tyr Phe Ser Leu Asp Thr Arg Phe Lys Val
                    35                          40                          45
Gly Thr Asp Gly Val Ile Thr Val Lys Arg Pro Leu Arg Phe His Asn
                    50                          55                          60
Pro Gln Ile His Phe Leu Val Tyr Ala Trp Asp Ser Thr Tyr Arg Lys
 65                          70                          75                          80
Phe Ser Thr Lys Val Thr Leu Asn Gly His His Arg Pro Pro
                    85                          90                          95
His Gln Ala Ser Val Ser Gly Ile Gln Ala Glu Leu Leu Thr Phe Pro
                    100                         105                         110
Asn Ser Ser Pro Gly Leu Arg Arg Gln Lys Arg
                    115                         120
```

<210> SEQ ID NO 2
<211> LENGTH: 132
<212> TYPE: PRT
<213> ORGANISM: Homo sapiens

<400> SEQUENCE: 2

```
Glu Ala Ser Gly Glu Ile Ala Leu Cys Lys Thr Gly Phe Pro Glu Asp
  1               5              10              15
Val Tyr Ser Ala Val Leu Ser Lys Asp Val His Glu Gly Gln Pro Leu
                    20                          25                          30
Leu Asn Val Phe Ser Asn Cys Asn Gly Lys Arg Lys Val Gln Tyr Glu
                    35                          40                          45
Ser Ser Glu Pro Ala Asp Phe Lys Val Asp Glu Asp Gly Met Val Tyr
                    50                          55                          60
Ala Val Arg Ser Phe Pro Leu Ser Ser Glu His Ala Lys Phe Leu Ile
 65                          70                          75                          80
Tyr Ala Gln Asp Lys Glu Thr Gln Glu Lys Trp Gln Lys Leu Ser Leu
                    85                          90                          95
Lys Pro Thr Leu Thr Glu Glu Ser Val Lys Glu Ser Ala Glu Val Glu
                    100                         105                         110
Glu Ile Val Phe Pro Arg Gln Phe Ser Lys His Ser Gly His Leu Gln
                    115                         120                         125
Arg Gln Lys Arg
          130
```

<210> SEQ ID NO 3
<211> LENGTH: 78
<212> TYPE: PRT
<213> ORGANISM: Homo sapiens

<400> SEQUENCE: 3

```
Cys Arg Ala Val Phe Arg Glu Ala Glu Val Thr Leu Glu Ala Gly Gly
  1               5              10              15
Ala Glu Gln Glu Pro Gly Gln Ala Leu Gly Lys Val Phe Met Gly Gln
                    20                          25                          30
Glu Pro Ala Leu Phe Ser Thr Asp Asn Asp Asp Phe Thr Val Arg Asn
                    35                          40                          45
Gly Glu Thr Val Gln Glu Arg Arg Ser Leu Lys Glu Arg Asn Pro Leu
                    50                          55                          60
Lys Ile Phe Pro Ser Lys Arg Ile Leu Arg Arg His Lys Arg
```

<210> SEQ ID NO 4
<211> LENGTH: 144
<212> TYPE: PRT
<213> ORGANISM: Homo sapiens

<400> SEQUENCE: 4

```
His Asn Glu Asp Leu Thr Thr Arg Glu Thr Cys Lys Ala Gly Phe Ser
 1               5                  10                  15
Glu Asp Asp Tyr Thr Ala Leu Ile Ser Gln Asn Ile Leu Glu Gly Glu
             20                  25                  30
Lys Leu Leu Gln Val Lys Ser Ser Cys Val Gly Thr Lys Gly Thr Gln
         35                  40                  45
Tyr Glu Thr Asn Ser Met Asp Phe Lys Gly Ala Asp Gly Thr Val Phe
     50                  55                  60
Ala Thr Arg Glu Leu Gln Val Pro Ser Glu Gln Val Ala Phe Thr Val
 65                  70                  75                  80
Thr Ala Trp Asp Ser Gln Thr Ala Glu Lys Trp Asp Ala Val Leu Val
                 85                  90                  95
Ala Gln Thr Ser Ser Pro His Ser Gly His Lys Pro Gln Lys Gly Lys
            100                 105                 110
Lys Val Val Ala Leu Asp Pro Ser Pro Pro Lys Asp Thr Leu Leu
        115                 120                 125
Pro Trp Pro Gln His Gln Asn Ala Asn Gly Leu Arg Arg Lys Arg
    130                 135                 140
```

<210> SEQ ID NO 5
<211> LENGTH: 22
<212> TYPE: PRT
<213> ORGANISM: Homo sapiens

<400> SEQUENCE: 5

```
Ala Gly Ala Asn Pro Ala Gln Arg Asp Thr His Ser Leu Leu Pro Thr
 1               5                  10                  15
His Arg Arg Gln Lys Arg
             20
```

<210> SEQ ID NO 6
<211> LENGTH: 35
<212> TYPE: PRT
<213> ORGANISM: Homo sapiens

<400> SEQUENCE: 6

```
Thr Leu Ser Thr Pro Leu Ser Lys Arg Thr Ser Gly Phe Pro Ala Lys
 1               5                  10                  15
Lys Arg Ala Leu Glu Leu Ser Gly Asn Ser Lys Asn Glu Leu Asn Arg
             20                  25                  30
Ser Lys Arg
         35
```

<210> SEQ ID NO 7
<211> LENGTH: 33
<212> TYPE: PRT
<213> ORGANISM: Homo sapiens

<400> SEQUENCE: 7

```
Thr Leu Ser Thr Pro Leu Ser Lys Arg Thr Ser Gly Phe Pro Ala Lys
 1               5                  10                  15
```

```
Lys Arg Ala Leu Glu Leu Ser Gly Asn Ser Lys Asn Glu Leu Asn Arg
            20                  25                  30

Ser

<210> SEQ ID NO 8
<211> LENGTH: 54
<212> TYPE: PRT
<213> ORGANISM: Homo sapiens

<400> SEQUENCE: 8

Met Leu Leu Asp Leu Trp Thr Pro Leu Ile Ile Leu Trp Ile Thr Leu
  1               5                  10                  15

Pro Pro Cys Ile Tyr Met Ala Pro Met Asn Gln Ser Gln Val Leu Met
            20                  25                  30

Ser Gly Ser Pro Leu Glu Leu Asn Ser Leu Gly Glu Gln Arg Ile
        35                  40                  45

Leu Asn Arg Ser Lys Arg
        50

<210> SEQ ID NO 9
<211> LENGTH: 31
<212> TYPE: PRT
<213> ORGANISM: Homo sapiens

<400> SEQUENCE: 9

Phe Ala Pro Glu Arg Arg Gly His Leu Arg Pro Ser Phe His Gly His
  1               5                  10                  15

His Glu Lys Gly Lys Glu Gly Gln Val Leu Gln Arg Ser Lys Arg
            20                  25                  30

<210> SEQ ID NO 10
<211> LENGTH: 26
<212> TYPE: PRT
<213> ORGANISM: Homo sapiens

<400> SEQUENCE: 10

Glu Arg Arg Gly His Leu Arg Pro Ser Phe His Gly His His Glu Lys
  1               5                  10                  15

Gly Lys Glu Gly Gln Val Leu Gln Arg Ser
            20                  25

<210> SEQ ID NO 11
<211> LENGTH: 31
<212> TYPE: PRT
<213> ORGANISM: Homo sapiens

<400> SEQUENCE: 11

Gln Pro Gln Pro Gln Gln Thr Leu Ala Thr Glu Pro Arg Glu Asn Val
  1               5                  10                  15

Ile His Leu Pro Gly Gln Arg Ser His Phe Gln Arg Val Lys Arg
            20                  25                  30

<210> SEQ ID NO 12
<211> LENGTH: 29
<212> TYPE: PRT
<213> ORGANISM: Homo sapiens

<400> SEQUENCE: 12

Gln Pro Gln Pro Gln Gln Thr Leu Ala Thr Glu Pro Arg Glu Asn Val
  1               5                  10                  15

Ile His Leu Pro Gly Gln Arg Ser His Phe Gln Arg Val
```

```
<210> SEQ ID NO 13
<211> LENGTH: 129
<212> TYPE: PRT
<213> ORGANISM: Homo sapiens

<400> SEQUENCE: 13

Glu Asp Leu Asp Cys Thr Pro Gly Phe Gln Gln Lys Val Phe His Ile
 1               5                  10                  15

Asn Gln Pro Ala Glu Phe Ile Glu Asp Gln Ser Ile Leu Asn Leu Thr
             20                  25                  30

Phe Ser Asp Cys Lys Gly Asn Asp Lys Leu Arg Tyr Glu Val Ser Ser
         35                  40                  45

Pro Tyr Phe Lys Val Asn Ser Asp Gly Gly Leu Val Ala Leu Arg Asn
     50                  55                  60

Ile Thr Ala Val Gly Lys Thr Leu Phe Val His Ala Arg Thr Pro His
 65                  70                  75                  80

Ala Glu Phe Asp Met Ala Glu Leu Val Ile Val Gly Gly Lys Asp Ile
                 85                  90                  95

Ser Leu Gln Asp Ile Phe Lys Phe Ala Arg Thr Ser Pro Val Pro Arg
                100                 105                 110

Gln Lys Arg Pro Ser Val Leu Leu Leu Ser Leu Phe Ser Leu Ala Cys
            115                 120                 125

Leu

<210> SEQ ID NO 14
<211> LENGTH: 39
<212> TYPE: PRT
<213> ORGANISM: Homo sapiens

<400> SEQUENCE: 14

Val Pro Gly Trp Arg Arg Pro Thr Thr Leu Tyr Pro Trp Arg Arg Ala
 1               5                  10                  15

Pro Ala Leu Ser Arg Val Arg Arg Ala Trp Val Ile Pro Pro Ile Ser
             20                  25                  30

Val Ser Glu Asn His Lys Arg
             35
```

CADHERIN DERIVED GROWTH FACTOR AND ITS USE

Figure 1:
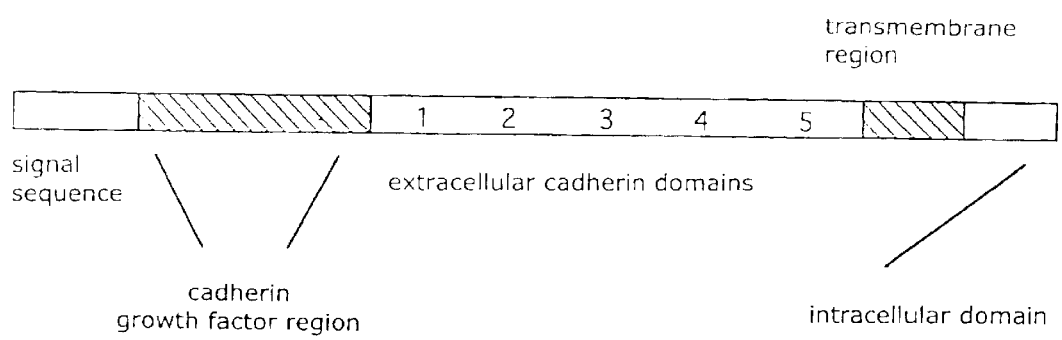

The present invention relates to peptides (proteins) having cell-proliferative, cell-differentiating and/or cell-protective properties referred to as cadherin-derived growth factor (CDGF), and their use.

It has been the object of the invention to provide peptides having cell-proliferative, cell-protective and/or cell-differentiating properties.

This object is achieved by peptides referred to as cadherin-derived growth factor (CDGF) the sequence of which corresponds to a partial sequence of a pre-pro-cadherin, said pre-pro-cadherin comprising the domains signal sequence, pro sequence, cadherin repeats, transmembrane region and intracellular domain, characterized in that the sequence of said peptide comprises the pro sequence, that at least one of the other domains of the pre-pro-cadherin is lacking, and that said peptide has cell-proliferative, cell-protective and/or cell-differentiating properties.

For example, the cell-proliferative activity can be determined on primary osteoblasts from rat calvarias, and the cell-protective and/or cell-differentiating activities can be determined on primary nerve cell cultures from spinal ganglia of chicken embryos.

In a preferred embodiment, the CDGF is a fragment of pro-cadherin, i.e., of pre-pro-cadherin truncated by the signal sequence.

More preferably, it is the N terminus of pro-cadherin, i.e., the part cleaved off during the processing of pro-cadherin into cadherin, or an N-terminally or C-terminally truncated fragment thereof.

Preferably, the CDGF comprises no cadherin repeats.

Preferred embodiments according to the invention are peptides having the sequence:

Cadherin-1 human (28–154) (SEQ ID NO: 1):
CHPGFDAESYTFTVPRRHLERGRVLGRVNFCTGR
QRTAYFSLDTRFKVGTDGVITVKR-
PLRFHNPQIHFLVYAWDSTYRKFSTKVTLNGH
HHRPPPHQASVSGIQAELLTFPNSSP-GLRRQKR Cadherin-2 human (24–15) (SEQ ID NO: 2):
EASGEIALCKTGFPEDVYSAVLSKDVHEGQPLLN
VFSNCNGKRKVQYESSEPADFKVD-
EDGMVYAVRSEPLSSEHAKFLIYAQDKETQEK
WQKLSLKPTLTEESVKESAEVEEIVF-
PRQFSKHSGHLQRQKR CadIicrin-3 human (27-107) (SEQ ID NO: 3):
CP.AV FREAFEVTLEAGGAEQEPGQAL-
GKVFMGQEPALFS
TDNDDFTVRNGETVQER-
RSLKERNPLKIFPSKRILRRHKR Cadherin-4 human (21-169) (SEQ ID NO: 4):
HNEDLTTRETCKAGFSEDDYTALISQNILEGEKL
LQVKSSCVGTKGTQYETNSMDFKG-
ADGTVFATRELQVPSEQVAFTVTAWDSQ-
TAEKWDAVLVAQTSSPHSGHKPQKGKKV-
VALDPSPPPKDTLLPWPQHQNANG Cadherin-5 human (26-47) (SEQ ID NO: 5):
AGANPAQRDTHSLLPTHRRQKR Cadherin-6 human (19-53) (SEQ ID NO: 6):
TLSTPLSKRTSGEPAKKRALELSGNSKNELNRSKR Cadherin-6 human (1'9–51) (SEQ ID NO: 7):
TLSTPLSKRTSGFPAKKRALELSGNSKNELNRS Cadherin-S human (SEQ ID NO: 8):
MLLDLWTPLIILWITLPPCIYMAPMN-
QSQVLMSGSPLELNSLGEEQRILNRSKR Cadherin-B human (Cadherin-11) Precursor (23–53) (SEQ ID NO: 9):
FAPERRGHLRPSFHGHHFKGKEGQVLQRSKR Cadherin-B human (Cadherin-11) Precursor (26–51) (SEQ ID NO: 10):
ERRGHLRPSFHGHHEKGKEGQVLQRS (OB-CDGF)

Cadherin-C human (Cadherin-12)-Brain-Cadherin Precuirsor (24–54) (SEQ ID NO: 11):
QPQPQQTLATEPRENVIHLPGQRSHFQRVKR Cadherin-C human (Cadherin-12)-Brain-Cadherin Precursor (24–52) (SEQ ID NO: 12):
QPQPQQTLATEPRENVIHLPGQRSHFQRV Cadherin-D human (Cadherin 13) (23–138) (SEQ ID NO: 13):
EDLDCTPGFQQKVFHINQPAEFIEDQSILNLTFSDC
KGNDKLRYEVSSPYFKVNSDGG-
LVALRNITAVGKTLFVHARTPHAEFDMAELVIV
GGKDISLQDIFKFARTSPVPRQKRP-
SVLLLSLFSLACL Cadherin-F human (Cadherin 14) (22–60) (SEQ ID NO: 14):
VPGWRRPTTLYPWRRAPALSRVR-
RAWVIPPISVSENHKR.

Preferably, the protein according to the invention is a protein obtainable from humans or a naturally occurring human variant thereof.

The present invention also relates to a novel protein which comprises parts of the amino acid sequence of CDGF. The invention preferably relates to a CDGF which contains the above represented amino acid sequences, but may also contain variants of these sequences. The term "variants" as used herein relates to sequences which are distinguished from the above represented amino acid sequences of CDGFs by the substitution, deletion and/or insertion of individual amino acids or short amino acid sequences.

The term "variants" encompasses both naturally occurring allelic variations of the CDGFs and proteins generated by recombinant DNA technology (especially by in vitro mutagenesis using chemically synthesized oligonucleotides) whose biological and/or immunological activities correspond to those of the CDGFs.

Conservative exchanges include, for example, Y for V or vice versa, K for S or vice versa, A for S or vice versa, D for E or vice versa, G for S or vice versa, R for Q or vice versa, R for A or vice versa, Q for K or vice versa.

According to the invention, there are also claimed nucleic acids coding for said peptides or derivatives, or those complementary to such nucleic acids. The nucleic acids may be, for example, DNA, RNA, PNA or nuclease-resistant analogues thereof. The nucleic acids according to the Invention are suitable for the in vivo expression of the CDGFs in a gene therapy, and as antisense nucleotides for reducing expression. The invention also relates to vectors containing said nucleic acids. The vectors are suitable, in particular, for expressing the peptide in genetically engineered organisms.

Further, the invention relates to antibodies directed against CDGF or derivatives thereof, and antagonists/inhibitors directed against CDGF, a derivative thereof, or any of the nucleic acids according to the invention. These substances are useful as medicaments for treating conditions related to an overexpression of CDGF, and for use in diagnostics.

The CDGFs, derivatives, compounds, nucleic acids, antibodies and/or antagonists/inhibitors according to the invention can be used as medicaments together with usual auxiliary agents. It is particularly preferred for the medicaments to be incorporated in suitable galenic formulations for oral, buccal, intravenous, intramuscular, intracutaneous, intrathecal, intranasal, topical administrations, and as an aerosol for transpulmonary administration.

The amount of medicament to be administered is preferably from 1 µg to 1 g per dosage unit per day.

The medicaments according to the invention are suitable for the treatment and prophylaxis of degenerative and metabolic diseases of the bones, such as osteoporosis, osteomalacia and osteopenia, of the pancreas, such as diabetes mellitus, of the muscles, such as muscular dystrophies, of the vessels, of the central and peripheral nervous systems, such as peripheral and central neuropathies, of the lungs, such as bronchial asthma, of the stomach, such as ulcer, and for the therapy and prophylaxis of inflammatory processes, disturbed inflammatory reactions, tumor diseases, and for wound and bone healing.

The diagnostic agent according to the invention contains poly- or mono-clonal antibodies against the peptide according to the invention, optionally in a labeled form, such as fluorescence-labeled or radioactively labeled forms, to be used in a per se known ELISA or RIA. The diagnostic agent according to the invention contains DNA, RNA and/or PNA, optionally in a modified and/or labeled form, for use in test systems known to those skilled in the art, such as PCR or fingerprinting.

The diagnostic agents are suitable for checking CDGF levels in tissues, in secretions and/or in body fluids, such as plasma, urine and cerebrospinal fluid, and as markers for functional disorders in bones, muscles, vessels, the nervous system, lymph organs, the gastrointestinal tract, the immune system, and of diabetes and inflammatory and neoplastic processes, and as a marker in cancer (tumor marker).

The CDGFs according to the invention and their derivatives can be obtained by isolation from hemofiltrate using cation-exchange extraction followed by elution of the adsorbed substances, renewed cation-exchange chromatography of the extract containing the peptides, and multistage reversed-phase chromatography. In total synthesis, the peptides according to the invention can be obtained by solid-phase synthesis in terms of Merrifield synthesis, or liquid-phase synthesis according to methods involving protected amino acids, known to those skilled in the art, followed by purification. The peptides according to the invention can also be prepared by methods of heterologous expression, known to those skilled in the art, using common biotechnological vectors.

For example, a peptide referred to as OB-CDGF was purified from human hemofiltrate by chromatographical methods and identified using a bioassay.

The peptide has a molecular mass of 3062.8 Da. To date, from the analysis of a cDNA, an OB-cadherin pre-pro sequence has been postulated. In this sequence derived from the cDNA, the peptide sequence according to the invention is located directly behind the putative signal sequence (see FIG. 1).

The biochemical characterization of the peptide according to the invention was effected by mass spectrometry and sequencing of the whole peptide. The sequence analysis of the biologically active peptide yielded the following- amino acid sequence for OB-CDGF:

ERRGHLRPSFHGHHEKGKEGQVLQRS (SEQ ID NO: 10)

In the ESI (electrospray ionization) mass spectrum of the OB-CDGF, its molecular weight was determined to be:

OB-CDGF, MW 3062.8 Da.

The peptide according to the invention can be obtained by a purification method starting from human hemofiltrate. This method according to DE 36 33 707, which discloses the recovery of proteins from hemofiltrate, was performed in a modified form.

Hemofiltrate is obtained in large amounts in the ultrafiltration of the blood of kidney disease sufferers. The human hemofiltrate is optionally diluted with water and acidified. Its pH value is preferably from 1.5 to 3.5, especially from 2.5 to 3.0. Thereafter, the hemofiltrate is passed over a cation exchanger, for example, a support material modified with sulfonic acid groups (Fraktogel SP-650 (M), Merck, Darmstadt). The peptides bound to the cation exchanger are eluted with a relatively highly concentrated salt solution. The ionic strength of the eluent is about that of a 0.5 to 1 M ammonium acetate solution.

The collected eluate is subjected to another cation exchange chromatography. This chromatography is preferably a stepwise elution with buffers of increasing pH values.

The fractions containing the peptide according to the invention are further purified by preparative reversed-phase chromatography followed by semi-preparative reversed-phase chromatography, for example, on C4-modified support materials. The purification level is preferably determined by analytical reversed-phase chromatography on C18-modified support materials.

The substance obtained by the chromatographic purification was subjected to structural elucidation. The molecular weight of the native peptide was determined using an electrospray mass spectrometer. The sequence analysis was effected through Edman degradation of the peptides and of chemically modified derivatives with an ABI 473 A sequencer.

Total synthesis was effected on usual solid phases according to Merrifield synthesis. The synthetic strategy and the construction of the peptide and derivatives thereof using the correspondingly protected amino acids are known to those skilled in the art.

The OB-CDGF and its cDNA, its gene and analogues, fragments and derivatives of said peptide, cDNA and gene as well as antibodies antagonizing the OB-CDGF can be used as medicaments.

FIG. 1 shows the domain structure of the cadherins.

Figure 2:
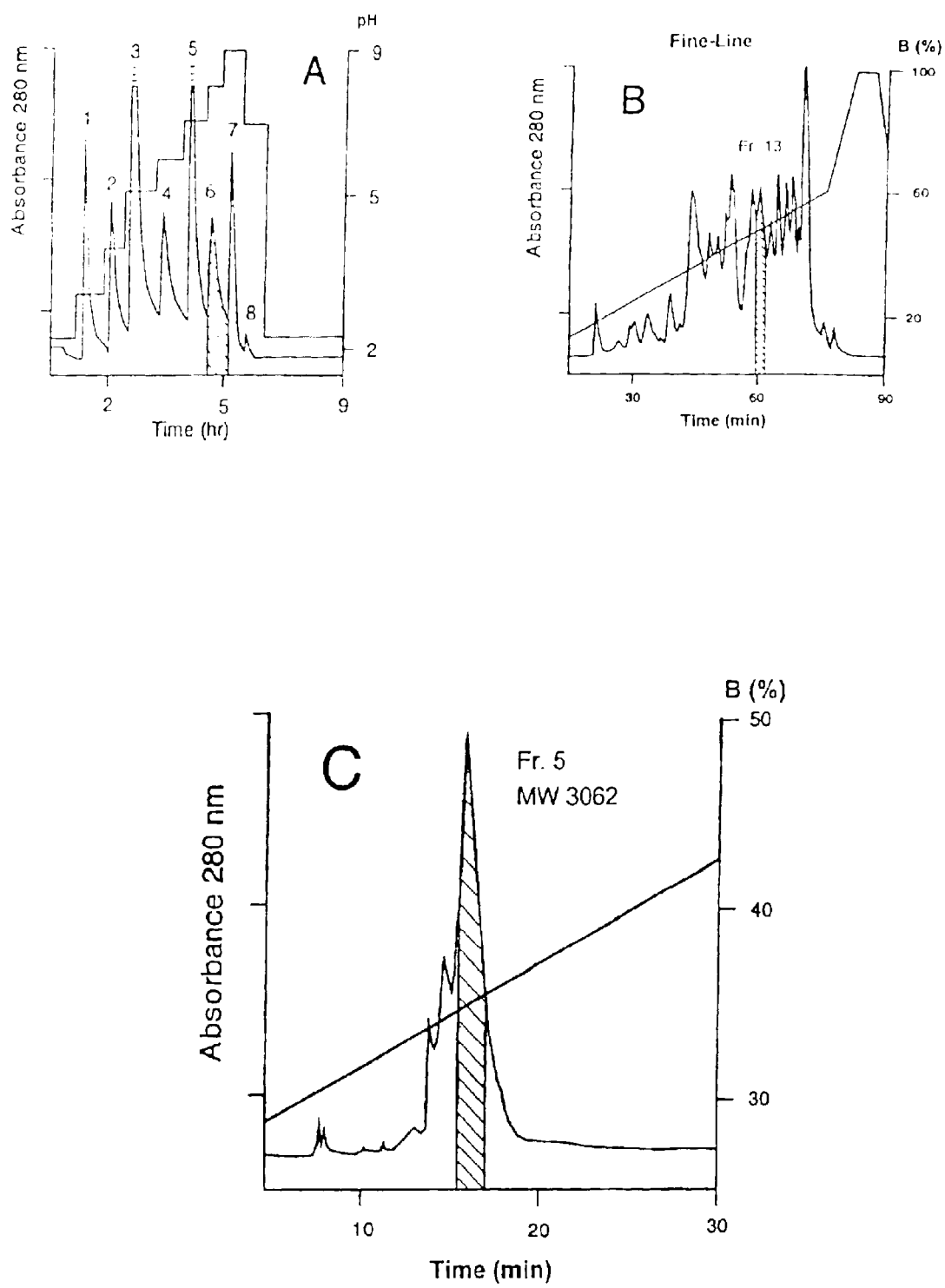

FIG. 2 shows the chromatograms from the isolation of OB-CDGF from hemofiltrate. Identification is effected by a proliferation assay on primary osteoblasts. Details of the purification can be seen from Example 1.

Figure 3:
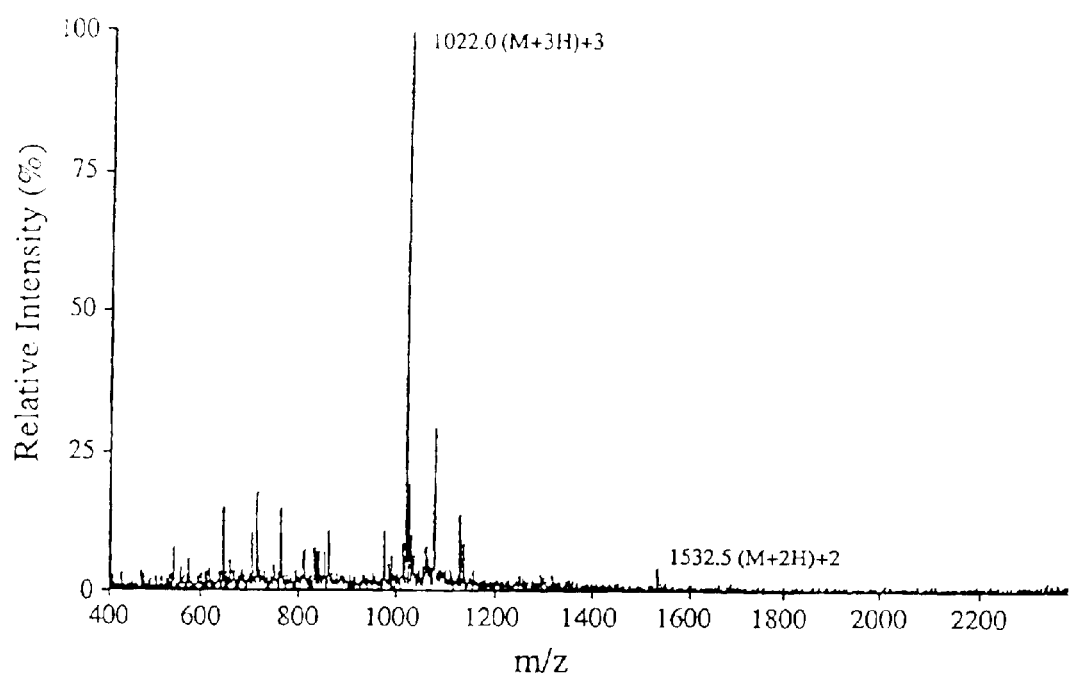

FIG. 3 shows the electrospray mass spectrum of the isolated OB-CDGF. From the twofold and threefold protonated ions, a molecular weight of 3,062 Dalton can be calculated.

Figure 4:
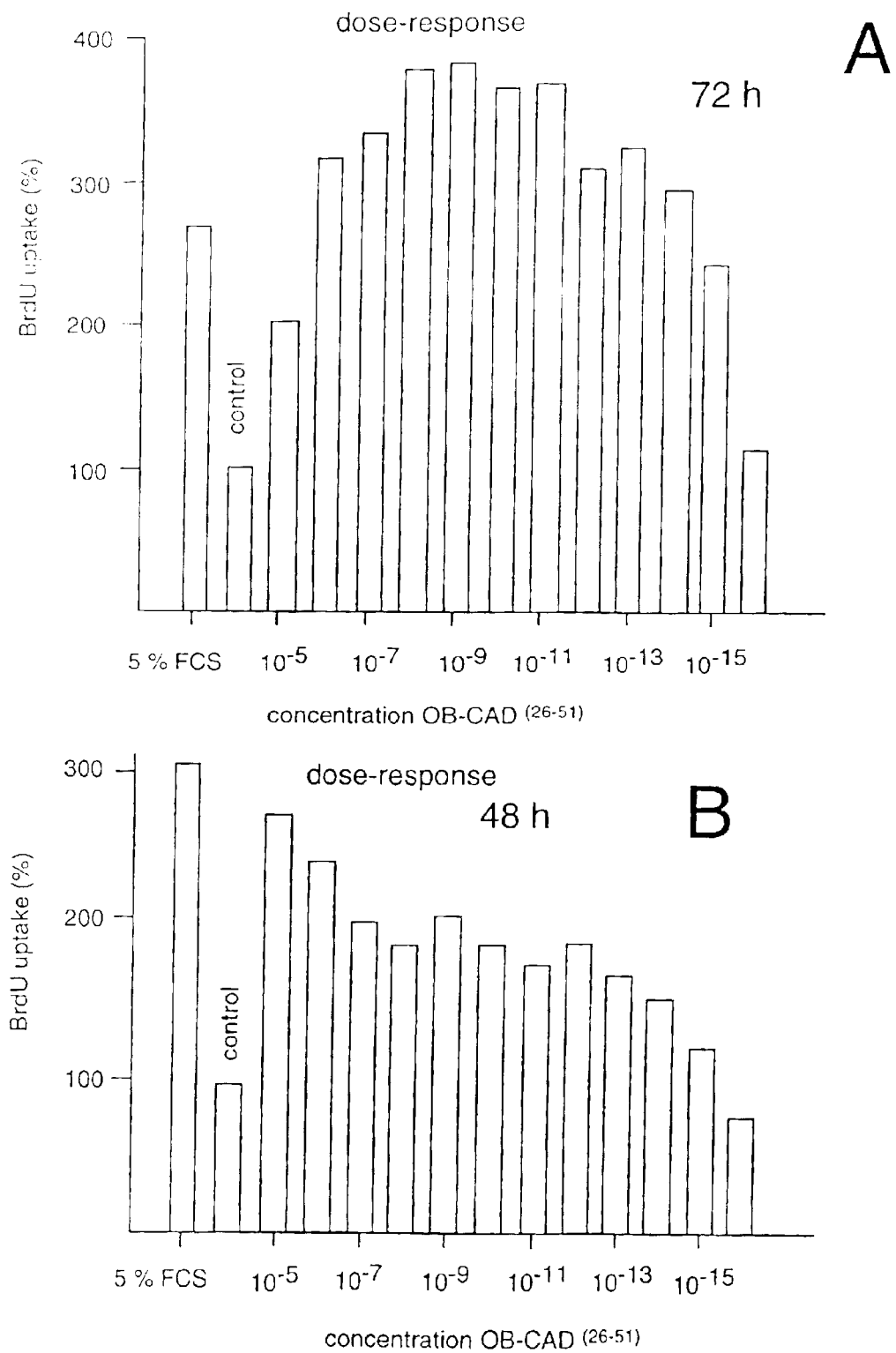

FIG. 4 shows the dose-effect curve of chemically synthesized OB-CDGF for its effect on the proliferation of primary bone cells. In FIG. 4a, the effect is shown for an incubation time of 72 hours, and in FIG. 4b, for an incubation time of 48 hours. The uptake of bromodeoxyuridine (BrdU) was measured. The incorporation of BrdU was measured using ELISA.

Figure 5:
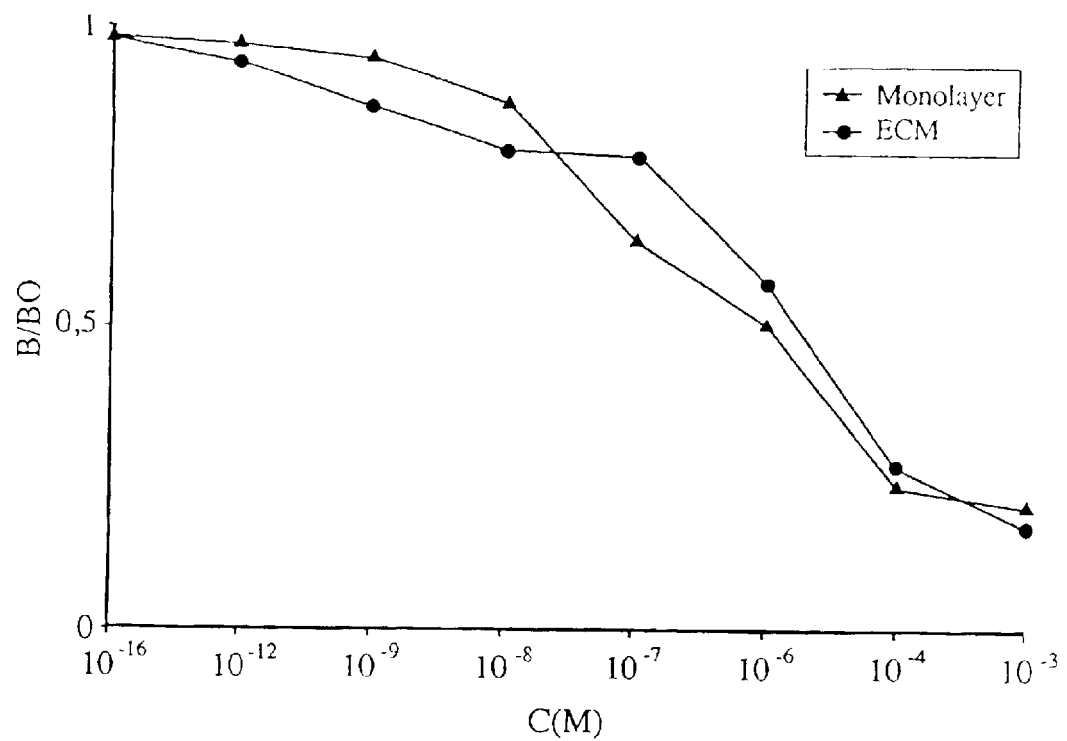

FIG. 5 shows the specific binding of iodine-labeled OB-CDGF to primary osteoblasts (monolayer) and to the extracellular matrix (ecm) of primary osteoblasts. The displacement of labeled OB-CDGF by unlabeled OB-CDGF is shown when the concentration of unlabeled OB-CDGF increases.

Figure 6:
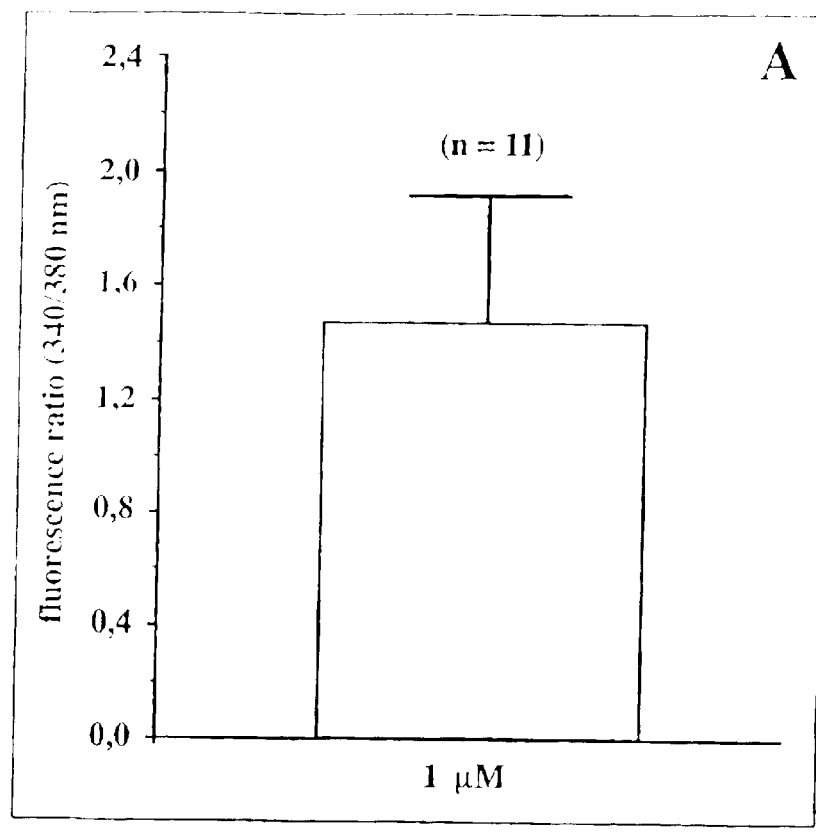
Figure 6:
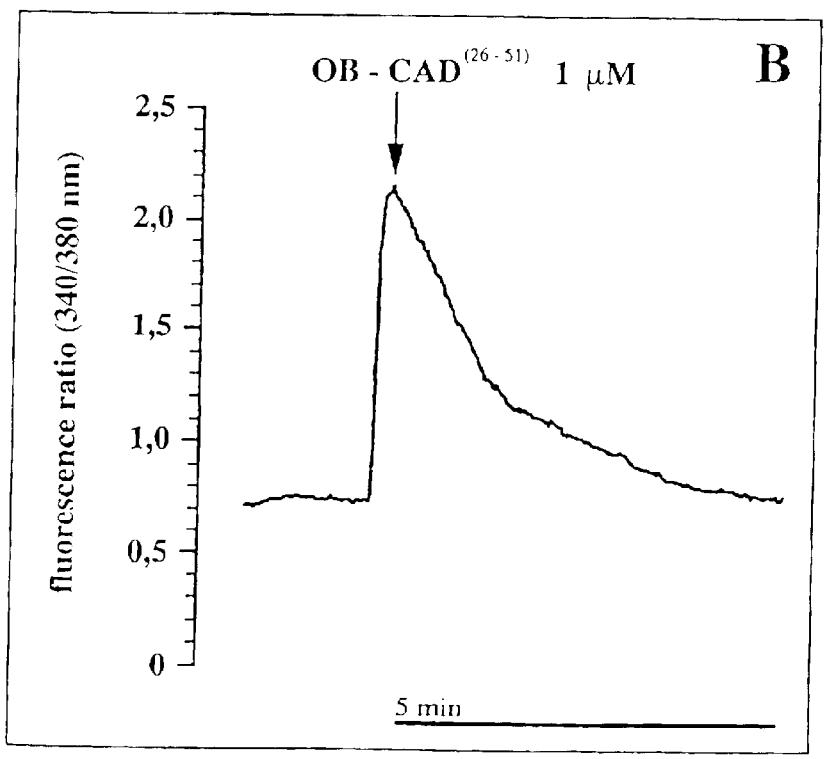

FIG. 6 shows the stimulation of primary ostebblasts by the addition of OB-CDGF. The intracellular calcium concentration increases upon the addition of OB-CDGF. The calcium content was measured in the presence of Fura-2 on individual cells under a fluorescence microscope.

Figure 7:
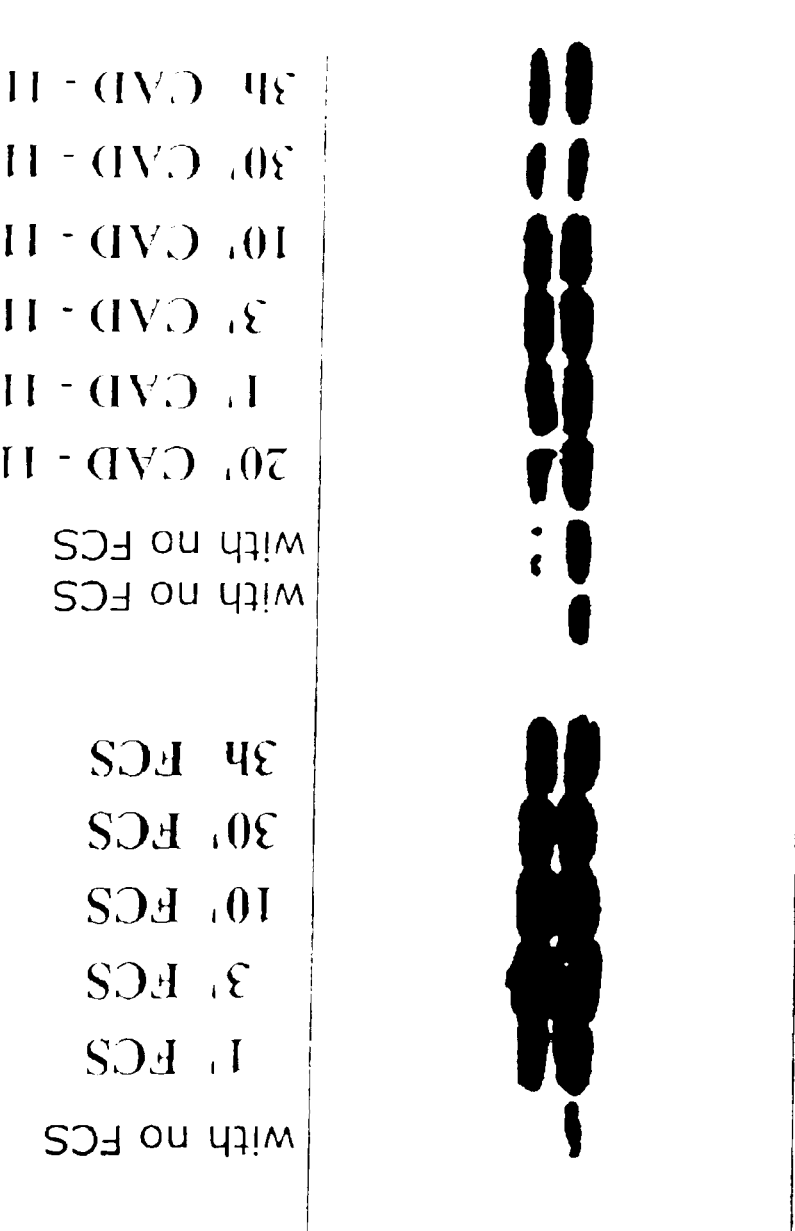

FIG. 7 is a Western blot which detects the intracellular MAP kinase activity. This activity is considered a parameter for the receptor- and calcium-mediated cellular response to OB-CDGF on primary osteoblasts. The upper band (46 kD) shows the concentration of MAP kinase upon stimulation with fetal calf serum FCS (left) or OB-CDGF (right) as a function of incubation time. The lower band shows an internal control for the cell lysis/Western blot.

The invention will be illustrated by the following Examples.

EXAMPLE 1

Hemofiltrate batch extraction 800 to 1,000 l of hemofiltrate are adjusted to pH 2.7 with HCl and diluted with water to a conductivity of 5,5 mS/cm, and applied to a strong cation-exchanger at a flow rate of 3 l/min.
Conditions of Chromatography:
column: Vantage VA 250 (Amicon, Witten)
column material: Fractogel TSK SP 650 (M), 25 cm×20 cm
flow rate: 3 l/min
detection: 280 nm, pH, conductivity
buffer A: hemofiltrate, pH 2.7, conductivity 5.5 mS/cm
buffer B: 0.5 M ammonium acetate
plant: Autopilot Chromatographiesystem (PerSeptive Biosystems, Wiesbaden)

After application of a total of 1,000 l of liquid over night, the column is washed with several column volumes of 5 mM HCl. The elution of the bound peptides is performed as a batch elution with 0.5 M ammonium acetate. Complete elution of the peptides is achieved with an increasing pH value (6.8 to 7.2) and increased conductivity (56 mS/cm) in about 5 l of eluate.

First Preparative Separation

The ammonium acetate eluates from the batch extraction are combined in amounts of 5,000 to 10,000 l of hemofiltrate peptide. After adjusting the pH to 2.7, the peptide extract is applied to the preparative cation-exchanger with admixing completely desalted water having a conductivity of 5.5 mS/cm.
Conditions of Chromatography:
column: Vantage 250 VA
column material: Fractogel TSK SP 650 (M), 25 cm×20 cm
flow rate: up to 3 l/min during application
0.5 to 1 l during elution
detection: 280 nm, pH, conductivity
sample: hemofiltrate, pH 2.7, conductivity 5.5 mS/cm
plant: Autopilot Chromatographiesystem (PerSeptive Biosystems, Wiesbaden)

After application of the raw extract over a period of 240 min, the column is washed with 0.01 M HCl until the conductivity has become below 1 mS/cm. Elution is effected in several steps with the following buffers:

| buffer (mS/cm) | pH value | buffer substances | conductivity |
| --- | --- | --- | --- |
| washing buffer | 2.0 | 0.01 M HCl | 1 |
| elution buffer 1 | 3.6 | 0.1 M citric acid 1-hydrate | 2.9 |
| elution buffer 2 | 4.5 | 0.1 M acetic acid + 0.1 M sodium acetate | 4.0 |
| elution buffer 3 | 5.0 | 0.1 M malic acid | 6.2 |
| elution buffer 4 | 5.6 | 0.1 M succinic acid | 6.1 |
| elution buffer 5 | 6.6 | 0.1 M NaH$_2$PO$_4$ | 4.9 |
| elution buffer 6 | 7.4 | 0.1 M NaH$_2$PO$_4$ | 6.7 |
| elution buffer 7 | 9.0 | 0.1 M ammonium carbonate | 6.7 |

Eluates 1–7 are referred to as pH pool I-VII. They are separately collected. Elution is performed until a new baseline is reached. For the individual pH pools I to VII, elution volumes of 10 to 25 l are reached. The chromatogram is shown in FIG. 2a.

Second Preparative Separation

The individual pH pools are separated by reversed-phase chromatography for fractionating and desalting at the same time.
Conditions of chromatography:
column: FineLine 100 (Pharmacia, Freiburg)
column material: Source RPC, 15 Fm 10×12.5 cm (FineLine 100)
flow rate: 150 ml/min (FineLine 100)
detection: 280 nm, conductivity, pH
buffer A: 10 mM HCl
buffer B: 80% acetonitrile in 10 mM HCl
gradient: 0–60% buffer B in 5 column volumes After application of the pH pools, the column is washed with buffer A. During the elution, fractions of 200 ml are collected. The chromatogram is shown in FIG. 2b. Aliquots of the fractions are tested in a bioassay. The fractions are freeze-dried and stored at −20° C.

Semipreparative Reversed-Phase C18 Chromatography

Fraction 13 from pH pool VI, which had been active in the bioassay, was separated through a semipreparative reversed-phase column. Fractions 5-7 contained the substance according to the invention.
Conditions of Chromatography:
column: 4.7 cm×30 cm steel column
column material: Vydac RP-C18 15-20 Fm, 300 A
buffer A: 0.1% TFA
buffer B: 0.1% TFA, 80% acetonitrile
gradient: 5-50% B in 45 min, 50-100% B in 10 min
flow rate: 42 ml/min
detection: 214 nm and 280 nm
chromatographic plant: BioCad
fractions: every 1.5 min from the start of the gradient
The chromatogram is shown in FIG. 2c.

Mass Determinations

All mass determinations of the native and synthetic peptides were performed on an electrospray mass spectrometer (ESI-MS). The molecular weights of the peptide were determined in accordance with the above shown molecular weights (MW). The mass spectrum is shown in FIG. 3.

Sequence Determination

The purified native peptide and the synthetically prepared peptide were analyzed by Edman degradation on an ABI 473 A Sequencer using the standard program. The samples were applied to a Polybrene membrane in amounts of between 100 and 400 pmol. In accordance with the results of mass determinations, the following amino acid sequence has been found:

ERRGHLRPSFHGHIHEKGKEGQVLQRS (SEQ ID NO: 10)

Data Base Comparison

A data base comparison was performed on the SwissProt and EMBL-Nukleinsäure data bases using the HUSAR program package. The sequence corresponds to the amino acids of the human cadherin-11 precursor as derived from the cDNA (osteoblast cadherin, propeptide, amino acids 26-51).

Resynthesis

Synthesis of the peptide having the sequence ERRGHL-RPSFHGHHEKGKEGQVLQRS (SEQ ID NO: 10) was performed according to the Merrifield solid phase method starting from protected Fmoc amino acids. The synthetic peptide was purified by using reversed-phase chromatography. The identity and purity of the substance were proven using mass spectrometry, sequence analysis and capillary zone electrophoresis.

Determination of the Biological Activity of OB-CDGF (Cell-Proliferative Effect)

The isolation of OB-CDGF was based on its biological activity in a proliferation assay of the primary osteoblasts. Thus, aliquots of each of the individual chromatographic stages described under Example 1 were freeze-dried and then subjected to a biological assay. The fractions which gave a positive signal were respectively subjected to further purification.

The assay measures the proliferation of the cells after having been kept in serum-free medium with 1 mg/ml bovine serum albumin, adding the samples and determining the incorporation of [$^3$H]thymidine or bromode-oxyuranosine (Brdu) after a further 48 hours. As a positive control, factors promoting bone growth, such as IGF or angiotensin, or fetal calf serum (FCS) are employed.

The experiments were performed by analogy with Pfeilschifter et al., Endocrinology 126, 703, 1990.

The recovery of primary osteoblasts was effected by sequential digestive separation from fetal rat calvarias using collagenase to obtain 5 cell fractions. The pooled cell fractions 3–5 were cultured in vitro. The culturing of the cells was performed in an incubator at a relative humidity of 95%, a $CO_2$ content of 5% and a temperature of 37° C. The examinations of the test substances were performed in cultures of the first, second or third cell passages.

For the examination, the cells were seeded in round-bottomed microtitration plates (MTP) at a number of cells of 7×103 cells (in 100 µl of culture medium) per well at least 95 hours before application of the test substances. Dulbec-co's MEM (plus 4.5 g/l glucose plus 3.7 g/l $NaHCO_3$ with no glutamine) supplemented with 5%/o fetal calf serum (FCS) and 5000 U/ml penicillin/streptomycin was used as the culture medium.

Immediately before the test substances were added to the cell culture, the medium was exchanged for 150 µl of medium containing 1 mg/ml bovine serum albumin (BSA) instead of FCS. Test substances were added to the BSA-containing medium in the desired concentrations. As a positive control, TGFD, (transforming growth factor Pi) was used in parallel tests in concentrations of from 0.1 to 0.2 ng/ml. For each (positive) control or substance concentration, determinations were performed in triplicate.

Incubation of the cell cultures with test substances was performed for 24 to 72 hours, in the last 3 hours in the additional presence of the thymidine probe (addition of 1 µCi of methyl[$^3$H]thymidine/MTP well in 20 µl of PBS solution).

At the end of the incubation time, the cell cultures were washed three times with 0.9% saline, and then 100 µl of liquid scintillator (OptiPhase Super-mix®, Wallac) was added to each well. Subsequently, the radioactivity incorporated in the DNA was measured in a liquid scintillation counter (1450 MicroBeta®, Wallac) in cpm.

In the evaluation, cell cultures which had obtained exclusively BSA-containing medium serve as controls (100%).

OB-CDGF has a dose-dependent growth-promoting effect on primary osteoblasts (bone cells). This biological activity has been established for both the native and the synthetically prepared peptides.

EXAMPLE 2

Determination of the biological activity of BR-CDGF

The peptide corresponding to the CDGF region of cadherin-12 (BR-cadherin; N-cadherin-2) having the amino acid sequence QPQPQQTLATEPREN-VIHLPGQRSHFQR (SEQ ID NO: 12), w%which has been synthesized by solid-phase synthesis as described under Example I for OB-CDGF, was tested for its survival-promoting, effect on primary cultures of neurons from spinal Langlia of chicken embryos.

The test model has the following design:

Primary Nerve Cell Cultures From Spinal Ganglia of Chicken Embryos (Embryo-Onal Development E10)

The preparation and cultivation is performed as described by Borasio G. D., John J., Wittinghofer A., Barde Y.-A., Sendtner M., Heumann R. (1989), Neuron 2, 1087–1096. To determine survival-promoting effects of active substances, determination of the cellular LDH level after an incubation time of 48 hours is employed. To this end, the culture medium is removed by tapping out the plate. Only the vital cells remain adhered to the bottom of the plate and can then be determined. To determine the LDH level, the LDH cytotoxicity test kit of Boehringer Mannheim (BM) is employed.

The cultures were used in duplicate in 96-well microtitration plates. On each plate, an NGF calibration curve is established in parallel, and the biological activity of the substances is expressed in pg/ml of NGF equivalents. As a low-molecular weight reference, the starurosporin derivative K252a is used in a parallel test in a concentration of 300 nmol/l.

The peptide exhibited a survival-promoting effect on these primary neurons in a concentration-dependent way. These cells are typical nerve cells; thus, BR-CDGF is a neuroprotective factor.

EXAMPLE 3

Determination of the biological activity of CAD6-CDGF (cell-protective effect)

The peptide corresponding to the CDGF region of cadherin-6 having the amino acid sequence TLSTPL-SKRTSGFPAKKRALELSGNSKNELNRS (SEQ ID NO: 7) which has been synthesized by solid-phase synthesis as described under Example for OB-CDGF, was tested for its surival promoting effect on primary cultures of neurons from spinal ganglia of chicken embryos. The test model has the design as described in Example 2.

The peptide exhibited a survival-promoting effect on these primary neurons in a concentration-dependent way.

EXAMPLE 4

Binding assay of labeled OB-CDGF to osteoblasts

The binding of the osteoproliferative peptides to neonatal rat osteoblast monolayers was effected with the use of $^{125}$j-labeled peptides. Chloramine T was used for iodination. The specific activity of the peptides was 100,000 cpm/ng. The binding studies were performed on confluent layers and the extracellular matrix of a first passage of neonatal rat osteoblasts. The cells were incubated for 24 hours in serum-containing medium and then washed four times with PBS and incubated for 2 hoursat 4° C. in 250 μl of the assay buffer (20 mM HEPES, 0.1 mg/ml BSA, pH 7.0) with 80,000 cpm of the iodine-labeled peptide in the presence of different concentrations of the unlabeled peptide. The incubation buffer was then removed, and the cells washed four times with cold PBS and solubilized with 1 M NaOH. The cell-bound activity was determined using a gamma counter. The corresponding experimental results are represented in FIG. 5. As the concentration of unlabeled OB-CDGF increases, the level of specifically bound labeled OB-CDGF is reduced.

EXAMPLE 5

Intracellular calcium release in primary osteoblasts

The intracellular signal chain for calcium$^{2+}$ is measured on individual osteoblast cells. The intracellular Ca$^{2+}$ activity of primary osteoblasts is measured with the Ca$^{2+}$-sensitive dye Fura-2 (Calbiochem, Bad Soden, Germany). The primary osteoblasts are cultured for one to three days on glass supports (diameter 30 mm) attached to a perfusion chamber of an inverted microscope (Axiomat IDC-UV, Zeiss, Gottingen, Germany). The cells were incubated in a modified Krebs-Henseleit buffer solution (KHB, composition 145 mM NaCl, 1.6 mM K$_2$HPO$_4$, 0.4 mM KH$_2$PO$_4$, 1.3 mM calcium gluconate, 1.0 mM MgCI2, 5.0 mM D-glucose, pH 7.4) for 10 min at 37 ° C. with 5 μM Fura-2/acetoxymethyl acetate dissolved in 0.1 g/l Pluronic F-127 (Sigma, Deisenhofen, Germany) in RPMI 1640 (PAA, Colbe, Germany).

The incubation is followed by an equilibration period of 10 to 15 min in which the cells are washed with KHB solution at 37° C. with a perfusion rate of about 5 ml/min. The Fura-2-charged primary osteoblasts are measured at 340, 360 and 380 nm with a high speed filter wheel (rotational speed 10 Hertz), a single-photon counter tube (Hamamatsu, Herrsching, Germany) and a xenon quartz lamp (XBO 75 W/OFR, Zeiss, Germany) as a light/impulse source. The Fura-2 emission is measured through a long-wave filter at 510 nm with an Ultrafluar 125 xglycerol immersion lens. All measurements are performed on single cells. The measuring field is selected by means of an adjustable hole of about 8 pm diameter. The ratio of photon emissions upon excitation at 340 and 380 nm is evaluated. The raw data are corrected for autofluorescence and noise. The thus obtained background value is subtracted from the measuring signals in each experiment. The raw data are calculated, and 10 neighboring data points are averaged to obtain a time resolution of 1 Hz. The fluorescence at 360 nm is used to test calcium activity. All samples are dissolved in a phosphate buffer prior to the experiment and measured for at least 1 to 2 minutes. The calibration of Ca$^{2+}$ is measured at the end of each experiment by incubating the cells with the Ca$^{2+}$ ionophore ionomycin (10 μmol, Sigma, Deisenhofen, Germany) in the presence of 1.3 mmol Ca$^{2+}$ or nominal absence thereof (5 mM ethylene glycol bis(p-aminoethyl ether)-N,N,N', N'-tetraacetic acid, in the presence of EGTA). Only calibrations with both maximum and minimum values are used for the determination of the Ca$^{2+}$ value. For the experiments in which the double calibration was unsuccessful, the average of all calibrations is used. The results are shown in FIG. 6.

EXAMPLE 6

As already shown under Example 5, intracellular calcium release can be induced on primary osteoblasts by incubation with CDGF. To further characterize this physiological response, the further intracellular signal pathway (downstream from calcium) was examined. One possible signal transduction cascade is the activation of MAP kinase, an enzyme which plays an essential role in the signal transduction from the cytoplasm into the nucleus. Signal transmission involves phosphorylation of the enzyme which can be detected with a specific antibody. Thus, this protein can be detected in a Western blot, which is a measure of both the phosphorylation and the expression due to the stimulus. Primary osteoblasts were incubated with cadherin or controls (FCS) for different periods of time. Expression of the enzyme (MAP kinase) in the cell was detected in the Western blot by the addition of the antibody. The results are represented in FIG. 7. It is clearly evident that no expression takes place without a stimulus such as FCS or OB-CDGF whereas a marked band of the expected size of MAP kinase appears (upper band) upon stimulation. The longer the stimulation with OB-CDGF, the more clearly could the band be discerned. This clearly shows that OB-CDGF leads to expression of intracellular MAP kinase. Therefrom, it can be concluded that CDGF acts through calcium in a receptor-mediated way, and the further signal processing proceeds via MAP kinase.

---

What is claimed is:

1. A purified peptide consisting of sequence ERRGHL-RPSFHGHHEKGKEGQVLQRS (OB-CDGF) (SEQ ID NO: 10).

2. A method comprising administering the peptide according to claim 1 to a person in need thereof to promote proliferation of osteoblasts.

3. A medicament containing the purified peptide according claim 1, together with auxiliary agents.

4. The medicament according to claim 3 in a form for administration selected from the group consisting of (a) a galenic formulation, wherein administration is by oral, intravenous, intramuscular, intracutaneous, or intrathecal route, and (b) an aerosol, wherein administration is transpulmonary.

5. A medicament containing the purified peptide according claim 1 in a galenic formulation.

6. A process for the preparation of the purified peptide according to claim 1 comprising isolating the peptide from a hemofiltrate using (i) cation-exchange extraction followed by (ii) elution of adsorbed substances to produce a first extract containing proteins, (iii) renewed cation-exchange chromatography of the first extract to produce a second extract containing proteins, and subjecting the second extract to multistage reversephase chromatography to produce the purified peptide protein; or synthesizing the peptide by solid-phase or liquid-phase synthesis; or recombinant, heterologous expression of DNA encoding the peptide.

* * * * *

UNITED STATES PATENT AND TRADEMARK OFFICE
CERTIFICATE OF CORRECTION

PATENT NO. : 6,809,175 B1
DATED : October 26, 2004
INVENTOR(S) : Forssmann et al.

It is certified that error appears in the above-identified patent and that said Letters Patent is hereby corrected as shown below:

Column 6,
Lines 21 and 42, change "Fm" to -- $\mu$m --.

Column 9,
Line 15, please change "hoursat" to -- hours at --.

Signed and Sealed this

Twenty-second Day of February, 2005

JON W. DUDAS
*Director of the United States Patent and Trademark Office*